US00PP10516P

United States Patent [19]

Lemon

[11] Patent Number: Plant 10,516

[45] Date of Patent: Jul. 21, 1998

[54] VARIETY OF GERANIUM PLANT NAMED 'OLYMPIA'

[75] Inventor: David Lemon, Lompoc, Calif.

[73] Assignee: John Bodger & Sons Company, So. El Monte, Calif.

[21] Appl. No.: 724,707

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,087 12/1989 Hofmann ..... Plt./87.12

P.P. 8,005 10/1992 Hofmann ..... Plt./87.12

*Primary Examiner*—Howard J. Locker

*Attorney, Agent, or Firm*—Fulwider Patton Lee & Utecht, LLP

[57] ABSTRACT

The cultivar is characterized by its medium green foliage and clear amethyst colored bloom. Its relatively strong growth habit, quick rooting time and continuous flowering provide for superb cuttings and also for quick recovery following wet weather conditions. The blooms exhibit good post-harvest quality.

2 Drawing Sheets

BACKGROUND OF THE NEW PLANT

The present invention comprises a new and distinct cultivar of *Pelargonium×hortorum* known by the varietal name Olympia (Oglevee No. 3105, Bodger No. 2GM 255-6). The new variety was discovered in a selective breeding program by David Lemon at Bodger Seeds, Ltd., Lompoc, Calif. The new variety is a selection from the crossing of Precious (U.S. Plant Pat. No. 8,005) which is characterized by a light orchid flower having a white eye, with Laura (U.S. Plant Pat. No. 7,087) which is characterized by a lavender pink flower with a white eye, these parents are distinguished from the claimed cultivar which has a light lavender pink flower without any eye.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa. using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWINGS

The accompanying drawings illustrate the new cultivar, the colors depicted being as nearly true as possible with color illustrations of this type.

Sheet 1 represents a side view of the new cultivar.

Sheet 2 is a view of the plant from above.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Mar. 14, 1996 under full light and greenhouse, and colorings were taken indoors under 200–220 foot candles of fluorescent cool white light using the R.H.S. Colour Chart of The Royal Horticultural Society of London.

The Plant

Classification:
- *Botanical.*—*Pelargonium×hortorum.*
- *Commercial.*—Zonal Florist's Geranium Olympia (Florist's geraniums are a high quality plant which also grows well outdoors).

Form: Semi-dwarf mound.
- *Height.*—17 cm above media surface.
- *Growth.*—Free basal branching.
- *Strength.*—No artificial support needed.

Foliage: Stalked leaf attachment, no zone present.

Leaves:
- *Size.*—10.25 cm across; fully expanded leaf.
- *Shape.*—Reniform; cordate base.
- *Margin.*—Crenate.
- *Texture.*—Slightly pubescent; slightly reflective.
- *Color.*—Top: Green group 137C. Bottom: Green group 147B. Zone: None.
- *Ribs and veins.*—Palmate venation: Color: Green group 146C.

Petioles:
- *Length.*—6.5–8.5 cm in length.
- *Color.*—Green group 146C.

Stem:
- *Color.*—Green group 146D.
- *Internodes.*—2.0 cm–5.0 cm.

The Bud (Umbel)

Shape: Upright; hemispherical cluster.

Size: 2.0–2.5 cm across (just one bud cracking color).

Inflorescence

Blooming habit: Semi-double; slow to shatter; continuous.

Borne: Umbel; florets on pedicel, pedicel on peduncle; 3.5–10.5 cm above canopy.

Closed florets:

Bud size.—0.8 cm in length; 0.9 cm in width.

Size:

*Fully open bloom/inflorescence.*—7.0–12.0 cm across.

Open florets:

*Form.*—Flat to cupped shape with largest part of petals curving inwardly while overlapping each other to offer a frilly appearance; about 20 florets per inflorescence appearing.

*Color.*—Upper surface: Purple group 78A is present at the outer edge of the petal and provides the majority of petal coloration; extreme base is hinted to white shade of White group 69A; with veins of Purple group 74A. Lower surface: Purple group 75B; veins of Purple group 74B; and outer edge has small areas of Purple group 74B at tip of petal. Eye: None prominent.

*Petals.*—6–9 in number; some twisted; separate, not united; margin entire.

*Open floret size.*—2.7–5.5 cm across.

*Texture and appearance.*—Satiny, appearance from a distance is a clear amethyst color above medium green foliage.

Petaloids:

*Quantity.*—4–9.

*Shape.*—Some flattened, some twisted and tubular, irregular in shape; some w/pollen attached (the structure may not change completely to a full petaloid form and may retain some anther characteristics).

*Color.*—*Top: Purple group* 78A. Bottom: Purple group 75B.

Pedicel:

*Length.*—4.3 cm–5.0 cm.

*Color.*—From sepals at Greyed-purple group 187A toward peduncle ranges from Greyed-purple group 187B to 187C.

Peduncle:

*Length.*—16 cm–28.2 cm.

*Color.*—Yellow-green group 144A.

Persistence:

*Disease resistance.*—Not known.

*Lasting quality.*—Unknown.

Reproductive Organs

Stamens:

*Anthers.*—2.5–3.0 mm.

*Filaments.*—Length: 8.0 mm — mostly found on petaloids. Color: Purple group 78A at upper surface; Purple group 75B on lower petaloid surface.

*Pollen.*—Color: Orange-red group 31A.

Pistils:

*Number.*—One; 5 parted.

*Length.*—1 cm.

*Stigma.*—Color: Purple, same color as pedicel.

*Style.*—Length: 3.5–4.0 mm.

Ovaries:

*Color.*—Green, pubescent, superior.

*Length.*—6.5–7.0 mm.

Fruit: None.

General Characteristics

Olympia adds a new color to the geranium market, not as pale of a lavender color as the Precious variety and not as dark as the Laura variety. Cutting production, rooting and finishing time and outdoor performance are all improved over both the Precious and Laura varieties. The large open floret appears single although it is a semi-double and is slow to shatter. The clear amethyst color is highlighted by the medium green foliage.

I claim:

1. A new and distinct variety of Geranium plant, substantially as shown and described.

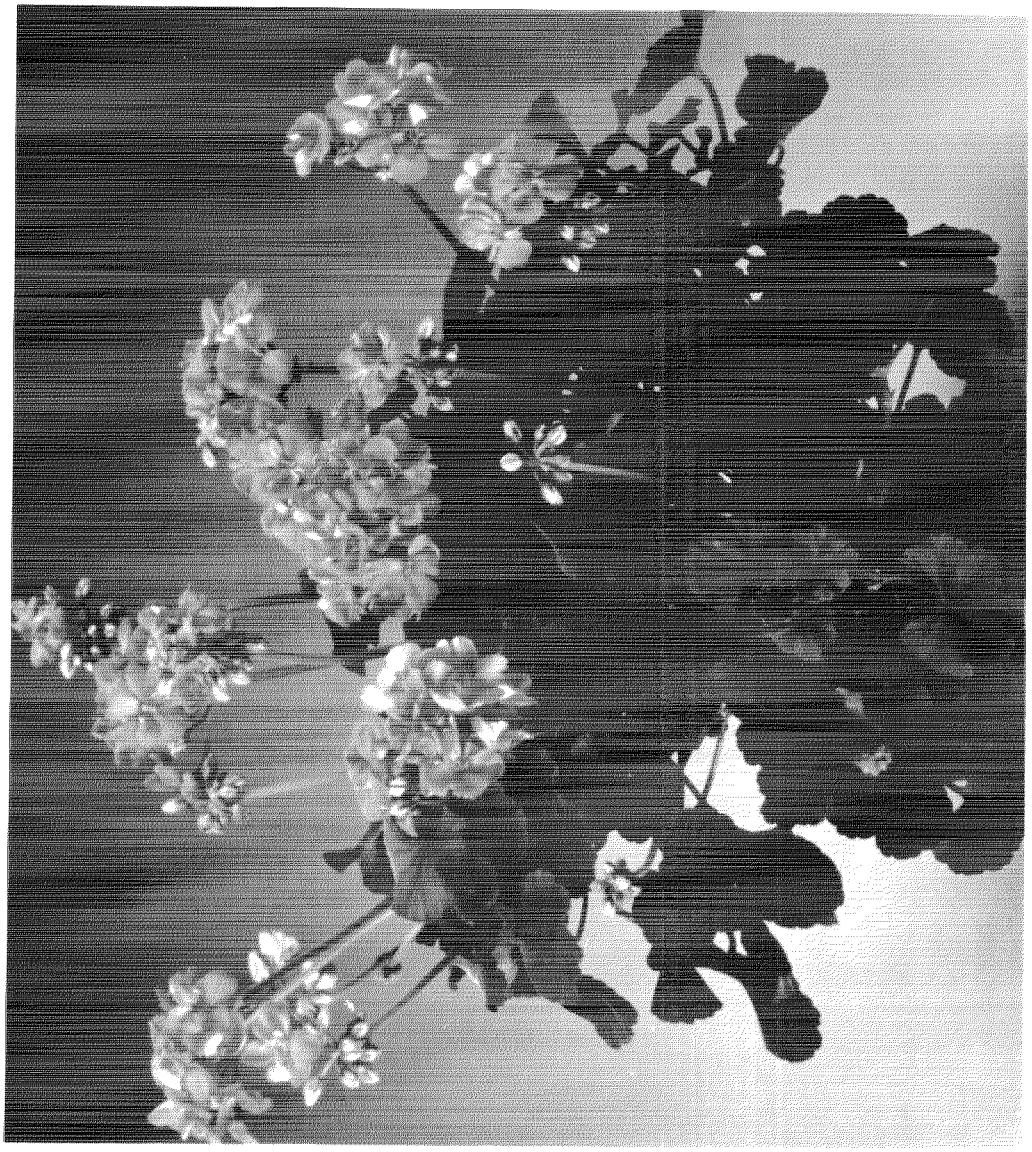

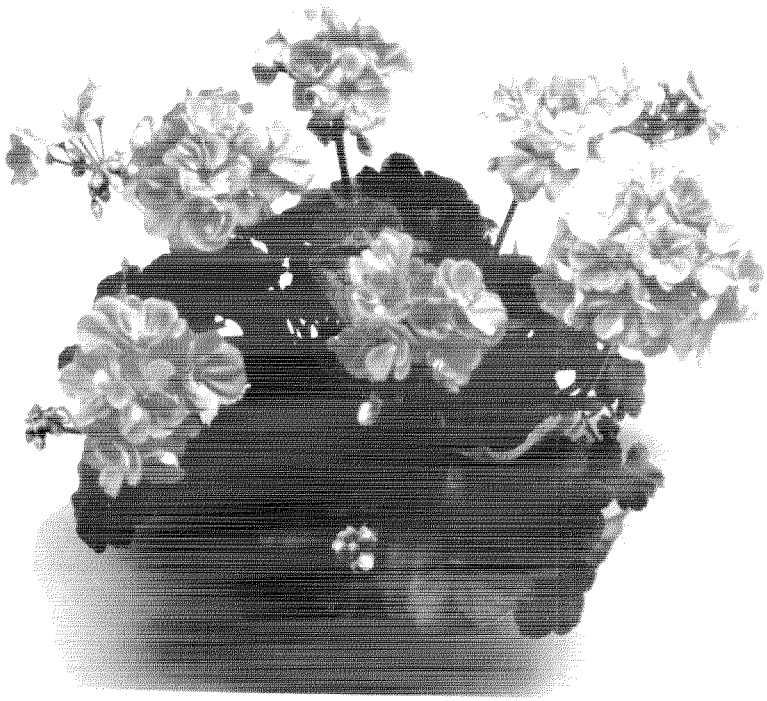

* * * * *